US008735621B2

(12) United States Patent
Corma Canós et al.

(10) Patent No.: US 8,735,621 B2
(45) Date of Patent: May 27, 2014

(54) PREPARATION OF CARBAMATES WITH SOLID CATALYSTS

(75) Inventors: Avelino Corma Canós, Valencia (ES); Raquel Juarez Marin, Valencia (ES); Hermenegildo Garcia Gomez, Valencia (ES)

(73) Assignees: Consejo Superior de Investigaciones Cientificas, Madrid (ES); Universidad Politecnica de Valencia, Valencia (ES)

( * ) Notice: Subject to any disclaimer, the term of this patent is extended or adjusted under 35 U.S.C. 154(b) by 516 days.

(21) Appl. No.: 13/002,439

(22) PCT Filed: Dec. 16, 2008

(86) PCT No.: PCT/ES2008/070232
§ 371 (c)(1),
(2), (4) Date: Jan. 26, 2011

(87) PCT Pub. No.: WO2010/000888
PCT Pub. Date: Jan. 7, 2010

(65) Prior Publication Data
US 2011/0124902 A1    May 26, 2011

(30) Foreign Application Priority Data
Jul. 4, 2008    (ES) .................. 200802101

(51) Int. Cl.
C07C 261/00    (2006.01)
C07C 269/00    (2006.01)
C07C 271/00    (2006.01)

(52) U.S. Cl.
USPC ........................................ 560/24

(58) Field of Classification Search
USPC ................. 560/24, 157, 345, 129, 132
See application file for complete search history.

(56) References Cited

U.S. PATENT DOCUMENTS

| 4,268,683 | A | | 5/1981 | Gurgiolo | |
| 5,220,069 | A | * | 6/1993 | King et al. | 564/393 |
| 5,686,645 | A | * | 11/1997 | Faraj | 560/24 |
| 5,698,731 | A | | 12/1997 | Bosetti | |
| 6,541,653 | B2 | | 4/2003 | Chuang | |
| 2005/0215427 | A1 | | 9/2005 | Suh | |
| 2005/0222450 | A1 | * | 10/2005 | Gupte et al. | 560/157 |
| 2005/0261125 | A1 | * | 11/2005 | Sagae | 502/325 |

FOREIGN PATENT DOCUMENTS

| CN | 1958156 | | 5/2007 |
| EP | 0048371 | * | 3/1982 |
| EP | 19820048371 A2 | * | 3/1982 |
| EP | 0323514 A1 | | 7/1989 |
| EP | 0570071 A1 | | 11/1993 |
| EP | 0752414 A1 | | 1/1997 |
| EP | 0881213 A2 | | 12/1998 |
| JP | 2002030062 | | 1/2002 |
| JP | 2006314885 A | * | 11/2006 |
| WO | WO 9855450 | | 12/1998 |
| WO | WO99/47493 | * | 9/1999 |
| WO | WO 9947493 | | 9/1999 |
| WO | WO 0156977 | | 8/2001 |
| WO | WO 2005063698 | | 7/2005 |
| WO | WO 2007015852 | | 2/2007 |

OTHER PUBLICATIONS

Kang et al. (Catalytic Performance of Supported PbO Catalysts for Synthesis of Methyl N-phenyl Carbamate from Aniline and Dimethyl Carbonate, Chinese Journal of Catalysis, vol. 28, No. 1, Jan. 2007, Table 1 p. 28).*
Kang et al. (Catalytic Performance of Supported PbO Catalysts for Synthesis of Methyl N-phenyl Carbamate from Aniline and Dimethyl Carbonate, Chinese Journal of Catalysis, vol. 28, No. 1, Jan. 2007, Translated on May 26, 2013 by The McElroy Translation Company).*
White et al. (Basic Energy Sciences Advisory Committee Subpanel Workshop Report, Opportunities for Catalysis in the 21st Century, 2002, pp. 1-47).*
Buysch et al. (Process for Producing N,0-Disubstituted Urethanes and Their Use as Starting Material for Producing Organic Isocyanates,EP0048371, 1982. All references to Buysch et al. are to a translation by FLS Inc. on Feb. 2013).*
English machine translation of JP2006314885 A, 2013.*
Shi et al., Preparation and Characterization of Polymer Immobilized Nano-Au Catalysts for Oxidative Carbonylation of Aniline and Its Derivatives, Science and Technology in Catalysis 2002, pp. 193-196.*
English machine translation of EP19820048371A2, 2013.*
Miyamura et al., Angew. Chem. Int. Ed., 46 : 4151-4154, 2007.
Baba et al., Applied Catalysis A: General, 227, 1-6, 2002.
Baba et al., Catalysis Letters, 82:3-4, 193-197, 2002.
Baba et al., Green Chemistry, 7, 159-165, 2005.
Carrettin et al., Advanced Synthesis & Catalysis, 348, 1283-1288, 2006.
Fu et al., Journal of Molecular Catalysis, 91, 399-405, 1994.

(Continued)

*Primary Examiner* — Brandon Fetterolf
*Assistant Examiner* — Blaine G Doletski
(74) *Attorney, Agent, or Firm* — Merchant & Gould P.C.

(57) ABSTRACT

Carbamate preparation process comprising, the reaction between at least:
  an amine or polyamines,
  an organic carbonate of formula $(OR)(OR')C=O$,
  a catalyst which is formed by at least a support selected from at least a metal oxide, a microporous material, a mesoporous material, an anionic laminar compound of hydrotalcite type or their derivatives or an organic polymer and which may further contain a metal from groups 8, 9, 10 and 11 of the periodical system.
The carbonates obtained can be transformed in their corresponding isocyanates.

17 Claims, No Drawings

(56) References Cited

OTHER PUBLICATIONS

Hashmi et al., Gold catalysis. Angew. Chem. Int. Ed., 45, 7896-7396, 2006.
Hashmi, Chemical Reviews, 107, 3180-3211, 2007.
Mallat et al., Chem. Rev., 104, 3037-3058, 2004.
Miyamura et al., Agnew. Chem., 119, 4229-4232, 2007.
Miyamura et al., Angew. Chem. Int. Ed., 46: 4151-4154, 2007.
Tundo et al., Pure Appl. Chem., 77:10, 1719-1725, 2005.
Vauthey et al., Tetrahedron Letters, 41, 6347-6350, 2000.
Wang et al., Journal of Chemical Technology and Biotechnology, 76, 857-861, 2001.
International Search Report of PCT/ES2008/070232 mailed Mar. 31, 2009.
Written Opinion of PCT/ES2008/070232 mailed Mar. 31, 2009.
International Preliminary Report of PCT/ES2008/070232 issued Feb. 8, 2011.

* cited by examiner

PREPARATION OF CARBAMATES WITH SOLID CATALYSTS

This application is a National Stage Application of PCT/ES2008/070232, filed 16 Dec. 2008, which claims benefit of Ser. No. 200802101, filed 4 Jul. 2008 in Spain and which applications are incorporated herein by reference. To the extent appropriate, a claim of priority is made to each of the above disclosed applications.

FIELD OF THE INVENTION

The present invention relates to a process to produce carbamates and their corresponding isocyanates by the reaction of aliphatic and aromatic amines or polyamines with organic carbonates in the presence of heterogeneous catalysts.

STATE OF THE ART

Organic carbamates can react with amines to give rise to carbamates which are compounds widely used in a large number of applications including pharmaceutical preparations, production of agricultural compounds (pesticides and herbicides). Of special relevance is the use of carbamates as precursors in the synthesis of isocyanates which can be used as monomers in the synthesis of polyurethanes.

One of the industrial processes for the synthesis of polyurethanes is based on producing isocyanates by the reaction of amines with phosgene. The toxicity of the phosgene determines that it is extremely convenient to look for alternatives to this reagent for the preparation of isocyanates. In this sense, one of the possible alternative channels to synthesize isocyanates consists of using carbamates as intermediates. The preparation of carbamates could be carried out by the reaction of organic carbonates with amines.

However, dialkyl carbonates can react with amines in two different ways. Either forming carbamates or by forming N-alkylation products. This second reaction acts by competing with the first and is undesirable when selective carbamate synthesis is pursued (Diagram 1).

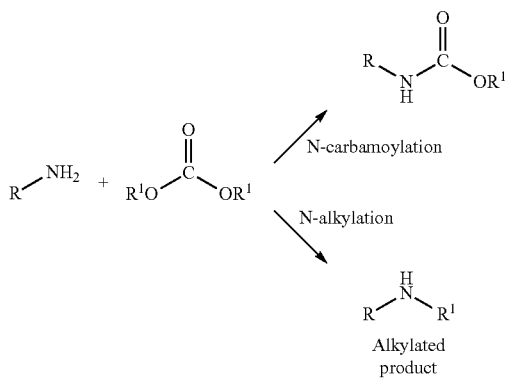

Diagram 1

The organic carbonate most widely used and which has been the object of greatest attention to due its accessibility is dimethyl carbonate, although other dialkyl carbonates and alicyclic carbonates may act similarly to dimethyl carbonate and may act in the presence of amines as alkylating or carbamoylating agents. Other organic carbonates that can be used are aromatic carbonates such as diphenylcarbonate or carbonates with groups polyfluorinated alkyls.

The reaction to form carbamates from organic carbonates (fundamentally dimethylcarbonate) and amines has been reported in the patent literature (U.S. Pat. Nos. 4,268,683 5,698,731, EP 0752414 B1, EP 0570071 B1, EP 0323514 B1, EP 0881213, WO 98/55450, WO 01/56977 as well as WO 2007/015852) and in open literature (J. Molec. Catal., 91, 399-405, 1994, Tetrahedron Letters, 41, 6347-6350, 2000, J. of Technology and Biotechnology, 76, 857-861, 2001, Applied Catalysis A: General, 227, 1-6, 2002, Catalysis Letters, 82, 193-197, 2002, Pure Appl. Chem., 77, 1719-1725, 2005 and Green Chemistry, 7, 159-165, 2005).

WO 99/47493 discloses a method for the preparation of organic carbamates by the reaction of alkyl amines and carbonates substituted with heteroatoms in the presence of organic salts of metals in inert supports or metal catalysts that form a precipitate during or after the reaction.

WO 2005/063698 proposes the use of basic solid catalysts for the synthesis of ureas and dimethylcarbonate or diphenylcarbonate.

The methods proposed in said art for producing carbamates by the reaction of amines and organic carbonates have a series of disadvantages. In first place, the use of soluble metal catalysts for said reaction is undesirable as they impurify the reaction products and their elimination is difficult and expensive to obtain carbamates with the purity required by their later industrial use. Furthermore, these catalysts generally lose their activity in the course of a reaction, and if recovered, they cannot be recycled to the process, which involves a relatively high cost of catalyst and the formation of metal residues undesirable from an environmental standpoint. Furthermore, some processes may produce an excessive quantity of N-Alkylation and/or low carbamoylation yield, further requiring high temperatures and/or relatively long reaction times.

DESCRIPTION OF THE INVENTION

The present invention relates to a carbamate preparation process comprising, the reaction between at least:
- an amine or polyamines,
- an organic carbonate of formula (OR)(OR')C=O,
- a catalyst which is formed by at least
    - a support selected from at least a metal oxide, a microporous material, a mesoporous material, an anionic laminar compound of hydrotalcite type or its derivatives or an organic polymer.

According to a preferred embodiment of the process of the invention, the catalyst further comprises a metal of groups 8, 9, 10 and 11 of the periodical system, more preferably 9, 10 and 11.

According to another preferred embodiment of the process of the invention, the catalyst support mentioned is a metal oxide which is selected from at least one of the following oxides, $Al_2O_3$, MgO, CaO, $Cu_xO_y$, $Co_xO_y$, $Fe_xO_y$, $Ce_xO_y$, $Cr_xO_y$, $ZrO_2$, $Y_2O_3$, and more preferably the support is $Ce_xO_y$, $ZrO_2$, $Fe_xO_y$ or $Y_2O_3$. Where x and y have any possible value, depending on of the state of oxidation of the metal containing said oxides.

The metal oxides may vary, for example, among amorphous, crystalline and structured, both laminar and with porosity in the range 0.7 to 100 nm. These oxides used as a support may contain two or more metals. The crystallographic phase can be pure or a mixture of several in any proportion. The particle size of the support may range from several nanometers to several microns. The oxide may be stoichiometric or the proportion between the metal and the oxygen differ from that expected based on the valence of the elements. These metal oxides also show an intrinsic catalytic activity promoting N-carbamoylation between aromatic amines and organic carbonates. Generally, the catalytic efficiency inherent to metal oxides in terms of reaction speed is improved with the deposition of gold nanoparticles.

The preferred particle size of said catalyst is between 1 and 50 nm.

According to another preferred embodiment, the catalyst support is at least a microporous material, more preferably a zeolytic material.

According to another preferred embodiment, the catalyst support is at least a structured mesoporous material.

According to another preferred embodiment, the catalyst support is at least an anionic laminar compound of hydrotalcite type or its derivatives.

According to another preferred embodiment, the catalyst support is at least an organic polymer. This organic polymer may be preferably a copolymer selected from styrene copolymer, 4-hydroxyethylstyrene copolymer and 4-glycidylstyrene copolymer. The organic polymer may also preferably be a polymer of dendrimer type. Among the dendrimers, preferred supports are those containing nitrogen atoms such as polyethyleneimines and polyamidoamines of third and fourth generation, preferably dendrimers of PAMAM type.

Also preferably the organic polymer may be a polymer of PEI type.

Preferably, the metal is selected from Fe, Cu, Ag, Pd, Pt, Ni, Co, Rh, Ir, Au or any mixture thereof, more preferably between Cu, Ag, Pd, Pt, Ni, Co, Rh, Ir, Au or any mixture thereof. This metal or any of its combinations may be in a preferred percentage between 0.01 and 10% by weight with respect to the catalyst, more preferably between 0.1 and 6%. Furthermore, the metal may have a particle size selected from 1 and 20 nm, more preferably between 2 and 10 nm.

According to a preferred embodiment, the metal of the catalyst described is gold.

In the present invention it has surprisingly been found that nanoparticulated metal oxides containing or not containing gold and gold nanoparticles on organic polymeric supports are capable of selectively catalysing the reaction between an amine or polyamine and an organic carbonate. The behaviour of the nanoparticulated metal oxides used as a support type of the gold nanoparticles or even the behaviour of the gold nanoparticles supported on different solids allows us to predict the catalytic behaviour in the reaction of amines with organic carbonates which, surprisingly and unexpectedly, based on the knowledge of the state of the art are extremely efficient and selective promoting the exclusive formation of the N-carbamoylation products.

As mentioned, in these cases wherein the metal is gold, this is preferably in the form of particles wherein the size of these gold nanoparticles is of vital importance in the catalytic activity, since the activity of the catalyst strongly decreases when the gold particles exceed a size of 20 nm. A more suitable particle size according to the process of the present invention would be between 1 and 20 nm, preferably between 2 and 10 nm. When the gold particles are supported, the nature of the support has influence on the activity and final selectivity of the catalyst. For example, when the gold particles are supported on active carbon the resulting material does not have the desired activity and selectivity for the carbamoylation reaction of aromatic amines with organic carbonates. A suitable support for the gold may be any of those previously described. In the specific case of metal oxides they also have catalytic activity in the carbamoylation reaction of aromatic amines. Thus, it has been observed in the present study that, preferably, the cerium oxide of nanometric particle size (>20 nm) shows a catalytic activity to promote the carbamoylation of aromatic amines. Likewise, the other nanometric metal oxides cited above show catalytic activity to promote the carbamoylation of aromatic amines. However, unexpectedly, this activity measured as reaction rate significantly increases to the N-carbamoylate derivative in the preferred embodiment wherein the cerium oxide is modified by absorption of gold nanoparticles.

It is important to bear in mind that the reaction conditions for carbamate formation according to the preferred embodiment wherein gold is used as metal in the catalyst are milder than those described to date. For example, to carry out the carbamoylation of aromatic amines temperatures between 20 and 200° C. can be used, and sufficient pressure to keep the reagents in liquid phase.

In some cases, the type of support shows less activity than the gold-containing catalysts. For example, cerium oxide, titanium oxide and iron oxide in the absence of gold nanoparticles give lower conversions than the analogues containing gold nanoparticles. In contrast, when gold is incorporated on any of said supports, especially in the case of metal oxides in quantities between 0.01 and 10% and more preferably between 0.1 and 6% by weight with respect to the catalyst, the activity and selectivity of the material is surprisingly greater. The behaviour of the catalyst in the reactions described cannot be deduced or derived from the knowledge of the state of the art in catalysis using metal oxide nanoparticles containing or not containing gold. (S Carrettin, M C Blanco, A Corma, A S K Hashmi: Heterogeneous gold-catalysed synthesis of phenols. Advanced Synthesis & Catalysis 348 (2006) 1283-88; ASK Hashmi, J Hutchings Graham: Gold catalysis. Angew. Chem. Int. Ed. 45 (2006) 7896-936; SAK Hashmi: Gold-catalyzed organic reactions. Chemical Reviews 107 (2007) 3180-211; T Mallat, A Baker: Chem. Rev. 104 (2004) 3037).

As gold supports, among others, organic polymers are mentioned in the present invention that interact with the gold nanoparticles by forces of type π-metal and which trap and immobilize the gold nanoparticles on interlinking the polymeric chains around the nanoparticles. For example, polystyrene can be used as support or a copolymer containing styrene and derivatives as monomers. A preferred embodiment is that where wherein three co-monomers(styrene, p-glycidylstyrene and p-2-hydroxyethylstyrene) form a polymeric support. The proportions of the monomers may vary in a wide range a preferred proportion being styrene/p-glycidylstyrene/p-2-hydroxyethylstyrene of 90/7/3.

Polystyrenes containing other neutral or positively or negatively charged co-monomers, polyacrylates and polyacrylamides are other polymers that can be used as support. Also, as previously mentioned, soluble polymers of dendrimer type can serve as supports of the gold nanoparticles.

Thus a preferred embodiment of the present invention consists of 0.1-4% by weight of gold with crystal size between 2 and 10 nm on cerium oxide art. The supports can be amorphous, but they may also have some type of structure. For example the supports can be laminar, such as, for example materials of hydrotalcite type or derived from mixed oxides of $Al_2O_3$, MgO, CaO, CuO, CoO, $Fe_2O_3$, $Ce_2O_3$, $Cr_2O_3$, $ZrO_2$, $Y_2O_3$.

The carbonates used according to the process of the present invention can be at least an organic carbonate of formula (OR)(OR')C=O, where R and R' may be selected from substituted alkyl groups between 1 and 20 carbon atoms, substituted aryl groups and non-substituted aryl groups.

In accordance with a preferred embodiment, R and R' are identical and are simple alkyl groups such as methyl or ethyl. Preferably, the carbonate is dimethyl carbonate or diethyl carbonate.

Among the cyclic carbonates, those derived from glycerine have special importance.

According to a preferred embodiment, R and R' can be fluorinated alkyl groups. According to this preferred embodiment, the organic carbonate may be selected from bis(2-fluoroethyl) carbonate, bis(3-fluoropropyl) carbonate, bis(2,2,2-trifluoroethyl) carbonate, bis(1,3-difluoro-2-propyl) carbonate, bis(1,1,1-trifluoro-2-propyl) carbonate, bis(2,2,3,3-tetrafluoro propyl) carbonate, bis(2,2,3,3,3-pentafluoropropyl) carbonate, bis(1-fluoro-2-butyl) carbonate, bis(2-fluoro-1-butyl) carbonate, bis(1-fluoro-2-methyl-2-propyl) carbonate, bis(2-fluoro-2-methyl-1-propyl) carbonate, bis(1H,1H,2H,2H-perfluoro-1-hexyl) carbonate, bis(perfluorooctyl) carbonate, bis(1,1,1,3,3,3-hexafluoro-2-propyl) carbonate, preferably bis(2,2,2-trifluoroethyl) carbonate.

Furthermore, the process of the present invention, comprises, among others, an aliphatic or aromatic amine or polyamines, which is preferably an amine of formula $R(NH_2)_n$ where R is selected from the group consisting of substituted or non-substituted alkyl with 1 to 20 carbon atoms, substituted or non-substituted aryl with 6 to 15 carbon atoms, substituted or non-substituted arylalkyl with 7 to 15 carbon atoms, substituted or non-substituted alkenyl with 2 to 20 carbon atoms, substituted or non-substituted alkynyl with 2 to 20 carbon atoms, substituted or non-substituted cycloalkyl with 3 to 20 carbon atoms, substituted or non-substituted cycloalkenyl with 4 to 20 carbon atoms and substituted or non-substituted cycloalkynyl with 5 to 20 carbon atoms; and n is 1, 2, 3, 4, 5 or 6.

Preferably, the amine or polyamine is selected from the group consisting of n-propylamine, isopropylamine, n-butylamine, n-hexylamine, n-octylamine, laurylamine, cyclopentylamine, cyclohexylamine, cyclooctylamine, 1,2-diaminoethane, 1,12-diaminododecane, 1,4-diaminocyclohexane, 1,3-bis(aminomethyl)cyclohexane, 1,4-bis(aminomethyl)cyclohexane, 2,4-hydrogenated diaminodiphenylmethane, hydrogenated toluenediamine, aniline, benzylamine, 2-aminotoluene, 4-aminotoluene, 2,4"-diaminodiphenylmethane, 4,4"-diaminodiphenylmethane, 2,2"-diaminodiphenylmethane, 2,4-toluenediamine, 2,6-toluenediamine, m-phenylendiamine, 1,5-diaminonaphthalene or any mixture thereof.

The process of the invention enables obtaining aliphatic and aromatic carbamates of amines and polyamines with a high yield and high purity whilst the heterogeneous character of the solid catalyst, preferably based on gold, facilitates its separation, recovery and reuse. The carbamates obtained according to the process of the present invention may furthermore be transformed into their corresponding isocyanate, for example by heat treatment or by reaction in basic medium or with the use of catalysts.

It is known that carbamates by thermolysis may undergo alcohol elimination reactions to yield isocyanates. This reaction generally requires the presence of catalysts. However, the presence of heteroatoms in the alkoxyl group of the carbamate or any functionality may facilitate its transformation into isocyanates. Of particular interest in the present invention is when the alkoxyl group contains one or more fluoride atoms. In this case, the carbamate may be easily transformed into isocyanates by elimination of the corresponding fluorinated alcohols, even in the absence of catalysts. Therefore, they are especially suitable for the synthesis of mono and polyisocyanates. Among the preferred polyisocyanates according to the present invention we have 2,4-toluene diisocyanate, isomeric diisocyanates derived from diaminophenylmethanes and the diisocyanates of hexamethylendiamine and other primary α,ω-diamines with a hydrocarbonated chain of between three and twelve carbon atoms.

Throughout the description and the claims, the word "comprises" and its variants do not aim to exclude other technical characteristics, additives, components or steps. For persons skilled in the art, other objects, advantages, and characteristics of the invention shall be partly gathered from the description and partly from practice of the invention. The following examples and drawings are provided by way of illustration and do not aim to be limiting of the present invention.

EXAMPLES

Non-limiting examples of the present invention shall be described below.

Example 1

Reaction of Dimethyl Carbonate with 2,4-Toluenediamine in the Presence of Gold Nanoparticles Supported on Cerium Oxide Dissolve 2,4-toluenediamine (0.1 g) in dimethyl carbonate (2.138 g) and to the mixture contained in a vial which can withstand pressure add 180 mg of a catalyst of gold on cerium (0.4% by weight of gold). The vial is hermetically sealed and is heated to 150° C. during 6 h. After 4 h, the mixture is left to cool and after reaching atmospheric pressure is opened. The filtered liquid contains 2,4-bis-(methoxycarbonylamino)toluene with a 91% yield. The catalyst is recovered by filtration, is washed with water at pH 10 and then acetone. The solid is filtered and is reused in a second reaction without appreciable change in the activity.

Example 2

Reaction of Dimethyl Carbonate with 2,4-Toluenediamine in the Presence of Cerium Oxide Dissolve 2,4-toluenediamine (0.1 g) in dimethyl carbonate (2.38 g) and to the mixture contained in a vial which can withstand pressure add 85 mg of cerium oxide. The vial is hermetically sealed and is heated to 150° C. during 6 h. After 4 h, the mixture is left to cool and after reaching atmospheric pressure is opened. The filtered liquid contains 2,4-bis(methoxycarbonylamino)toluene in a 37% yield accompanied by methoxycarbonylaminotoluenes (ortho and para isomers) in 54%. Therefore, the comparison of the catalytic data of examples 1 and 2 demonstrates the effect of the deposition of gold nanoparticles on the catalytic efficiency of the support increasing the activity of the support towards the N,N"-dicarbamoylation product. However, longer reaction times (22 h) gives rise to the formation of 2,4-bis(methoxycarbonylamino)toluene in a 95% yield.

Example 3

Reaction of Diethyl Carbonate with Aniline in the Presence of Gold Nanoparticles Supported on Cerium Oxide Dissolve aniline (0.051 g) in diethyl carbonate (1.95 g) and to the mixture contained in a vial which can withstand pressure add 190 mg of a catalyst of gold on cerium oxide (1.6% by weight of gold). The vial is hermetically sealed and is heated to 150° C. during 6 h. After 6 h, the mixture is left to cool and after reaching atmospheric pressure is opened. The filtered liquid contains N-(methoxycarbonyl)aniline in a 98% yield. The catalyst is recovered by filtration, is washed with water at pH 10 and then acetone. The solid is filtered and reused in a second reaction without appreciable change in the activity.

Example 4

Preparation of Bis(O-2,2,2-Trifluoroethyl)Carbamate of 2,4-Toluenediamine [2,4-Bis(2,2,2-Trifluoroethyloxycarbonylamino)Toluene] Using Gold Nanoparticles in a Copolymer Derived from Styrene as Catalyst The styrene copolymer, 4-(2-hydroxyethoxy)styrene and 4-glycidylstyrene containing gold nanoparticles is prepared in accordance with the state of the art and particularly as described in reference (H Miyamura, R Matsubara, Y Miyazaki, S Kobayashi: Aerobic oxidation of alcohols at room temperature and atmospheric conditions catalyzed by reusable gold nanoclusters stabilized by the benzene rings of polystyrene derivatives. Angewandte Chemie-International Edition 46 (2007) 4151-54). 2,4-Toluenediamine (1.22 g) is added to bis(2,2,2-trifluoroethyl) carbonate (67.8 g, 30 equivalents) and the mixture is heated to 60° C. When the mixture reaches this temperature the copolymer containing gold nanoparticles in 1% by weight is added. The mixture is magnetically stirred during 1 h. After that time, the mixture is left to cool at ambient temperature and the solid is separated by filtration. The liquid phase is left to crystallize at ambient temperature, collecting a solid that corresponds to bis(O-2,2,2-trifluoroethyl)carbamate of 2,4-toluenediamine with a degree of purity over 90%. The yield of the reaction is 95% with respect to 2,4-toluenediamine. The carbamate can be crystallized in 2,2,2-trifluoroethanol. Physical properties: melting point 119° C.; IR wave number: 3286, 2981, 1708, 1546, 1772, 1087 cm$^{-1}$, NMR $^1$H δ: 2.35, 4.60, 7.02, 7.26, 7.90 ppm.

Example 5

Synthesis of Bis(O-2,2,2-Trifluoroethyl) Carbamate of 4,4'-Diaminodiphenylmethane sing Gold Nanoparticles Supported on Cerium Oxide as Catalyst 4,4'-Diaminodiphenylmethane (1.98 g) is added to bis(2, 2,2-trifluoroethyl) carbonate (67.8 g, 30 equivalents) and the mixture is heated to 60° C. When the mixture reaches this temperature add the catalyst consisting of gold nanoparticles supported on cerium oxide (100 mg, 0.44% by weight of gold). The suspension is magnetically stirred during 1 h. After that time, the mixture is left to cool at ambient temperature and the solid is separated by filtration. The liquid phase is left to crystallize at ambient temperature, collecting a solid that corresponds to bis(O-2,2,2-trifluoroethyl) carbamate of 4,4'-diaminodiphenylmethane with a degree of purity over 90%. The yield of the reaction is 90% with respect to 4,4'-diaminodiphenylmethane. The carbamate can be crystallized in 2,2,2-trifluoroethanol.

Example 6

Reaction of Dimethyl Carbonate with 2,4-Toluenediamine in the Presence of Gold Nanoparticles Supported on Titanium Oxide Dissolve 2,4-toluenediamine (0.145 g) in dimethyl carbonate (2.138 g) and to the mixture contained in a vial which can withstand pressure add 12.8 mg of a catalyst of gold on titanium oxide (P-25, 80% anatase, 1.5% by weight of gold). The vial is hermetically sealed and is heated to 130° C. during 20 h. After 20 h, the mixture is left to cool and after reaching atmospheric pressure is opened. The filtered liquid contains 2,4-(N,N''-dimethylamino)toluene with a 15% yield, with 2,4-diaminotoluene remaining without reacting (83%).

Example 7

Formation of Toluene Diisocyanate from Bis(O-Trifluoroethyl and Toluenediamine) Carbamate A solution of bis(toluenediamine) carbamate (1 g) with trifluoroethyl groups in xylenes is heated to 150° C. in the absence of catalyst for a space of 2 h. After that time the reaction mixture contains toluene diisocyanate in a yield of 70%.

Example 8

Reaction of Dimethyl Carbonate with 2,4-Toluenediamine in the Presence of Platinum Nanoparticles Supported on Cerium Oxide Dissolve 2,4-toluenediamine (0.1 g) in dimethyl carbonate (2.138 g) and to the mixture contained in a vial which can withstand pressure add 180 mg of a catalyst of platinum on cerium (0.44% by weight of platinum). This catalyst is prepared from 100 ml of an aqueous solution containing 9.25 mg of hydrated tetrachloroplatinic acid which is neutralized to pH 10 with an aqueous solution of 0.2 N NaOH. Next, nanoparticulated cerium oxide in powder is added, readjusting the pH to a value of 10 with the NaOH solution. The suspension is magnetically stirred throughout the night. Then the solid is filtered, it is thoroughly washed with milliQ water and is dried at 100° C. in an oven. Once dry, the solid is poured into a flask containing 1-phenylethanol at a temperature of 160° C. under magnetic stirring. The suspension is kept at 160° C. during 20 minutes and the solid is then filtered, consecutively extracted with acetone and water, then being ready for its use as carbamoylation catalyst.

The vial containing toluenediamine, dimethyl carbonate and the platinum catalysis is hermetically sealed and is heated to 150° C. during 22 h. After this time, the mixture is left to cool and after reaching atmospheric pressure is opened. The filtered liquid contains 2,4-bis-(methoxycarbonylamino) toluene with a 53% yield. Furthermore, the reaction mixture contains 27% of the para and ortho isomers of the mono carbamoylate derivative. The reaction mixture is free from N-methylation compounds. The catalyst is recovered by filtration, is washed with water at pH 10 and then acetone. The solid is filtered and reused in a second reaction without appreciable change in the activity.

Example 9

Reaction of Dimethyl Carbonate with 2,4-Toluenediamine in the Presence of Palladium Nanoparticles Supported on Cerium Oxide The palladium catalyst at 0.44% by weight used in the present example is prepared following the process described for platinum supported on cerium, but using 20.1 mg of the bis(acetonitrile)chloropalladium(II) complex as substrate.

180 mg of this palladium catalyst is added to a 2,4-toluenediamine (0.1 g) solution in dimethyl carbonate (2.138 g) contained in a vial that can withstand pressure. The vial is hermetically sealed and is heated to 150° C. After 22 h, the mixture is left to cool and after reaching atmospheric pressure is opened. The filtered liquid contains 2,4-bis-(methoxycarbonylamino)toluene in a 57% yield. Furthermore, the reaction mixture contains 30% of the para and ortho isomers of the mono carbamoylate derivative. The reaction mixture is free from N-methylation compounds. The catalyst is recovered by filtration, is washed with water at pH 10 and then acetone. The solid is filtered and is reused in a second reaction without appreciable change in the activity.

Example 10

Reaction of Dimethyl Carbonate with 2,4-Toluenediamine in the Presence of Silver Nanoparticles Supported on Cerium Oxide The catalyst constituted by silver nanoparticles 0.44% by weight supported on nanoparticulated cerium oxide is prepared following the process described for the catalyst of platinum supported on cerium, but using 10.1 mg of the silver nitrate as substrate.

180 mg of this silver catalyst are added to a 2,4-toluenediamine (0.1 g) solution in dimethyl carbonate (2.138 g) contained in a vial which can withstand pressure. The vial is hermetically sealed and is heated to 150° C. After 22 h, the mixture is left to cool and after reaching atmospheric pressure is opened. The filtered liquid contains 2,4-bis-(methoxycarbonylamino)toluene in a 16% yield. Furthermore, the reaction mixture contains 3% of the para and ortho isomers of the mono carbamoylate derivative. The reaction mixture is free from N-methylation compounds. The catalyst is recovered by filtration, is washed with water at pH 10 and then acetone. The solid is filtered and is reused in a second reaction without appreciable change in the activity.

Example 11

Reaction of Dimethyl Carbonate with 2,4-Toluenediamine in the Presence of Copper Nanoparticles Supported on Cerium Oxide The catalyst constituted by copper nanoparticles at 1% by weight supported on nanoparticulated cerium oxide is prepared following the process described for the catalyst of platinum supported on cerium, but using 23.8 mg of the copper acetate as substrate.

180 mg of this copper catalyst are added to a solution of 2,4-toluenediamine (0.1 g) in dimethyl carbonate (2.138 g) contained in a vial that can withstand pressure. The vial is hermetically sealed and is heated to 150° C. After 22 h, the mixture is left to cool and after reaching atmospheric pressure is opened. The filtered liquid contains 2,4-bis-(methoxycarbonylamino)toluene in a 69% yield. Furthermore, the reaction mixture contains 29% of the para and ortho isomers of the mono carbamoylate derivative. The reaction mixture is free from N-methylation compounds. The catalyst is recovered by filtration, is washed with water at pH 10 and then acetone. The solid is filtered and is reused in a second reaction without appreciable change in the activity.

Example 12

Reaction of Dimethyl Carbonate with 2,4-Toluenediamine in the Presence of Fe/TiO$_2$ Nanoparticles A catalyst of titanium oxide doped with Fe is prepared from titanium oxide Degussa P25 (10 g. This titanium oxide is impregnated with a solution of 0.1715 g of iron nitrate in 10 ml of milliQ water. The mixture is stirred at 50° C. until the liquid phase evaporates and then the solid is dried at 100° C. and is calcined at 400° C. in an oven for 5 hours. The final iron content measured by atomic absorption was 0.56% by weight. With this catalyst (148 mg) the reaction of 2,4-toluenediamine (0.11 g) in dimethyl carbonate (2.2 g) is carried out in a vial which can withstand pressure during 15 h.

After this time, the mixture is left to cool and after reaching atmospheric pressure is opened. The filtered liquid contains a mixture where the mono carbamoylation has occurred in a percentage of 74%.

Example 13

Reaction of Dimethyl Carbonate with 2,4-Toluenediamine in the Presence of Fe/CeO$_2$ Nanoparticles The catalyst of this example is prepared from nanoparticulated cerium oxide identical to that used in the preparation of the Au/CeO$_2$ catalyst. It is prepared as follows: a solution of 24.2 mg of iron chloride hexahydrate in 100 ml of milliQ water. The pH of the solution is adjusted to 10 with a solution of 0.2 M NaOH. Once the solution has stabilized, add 1 g of nanoparticulated CeO$_2$, readjusting the pH again to its value of 10. The suspension is stirred during 8 h. After this time, the solid is filtered and washed thoroughly with MilliQ water until observing a negative chloride test in water with silver nitrate as reagent. The volume used in the preparation of 1 g of Fe/CeO$_2$ catalyst was 2 L. The solid is dried in the oven at 100° C. and it is then added to a flask with 10 g of 1-phenylethanol at a temperature of 160° C. The suspension is kept under stirring at this temperature during 30 minutes. The solid is filtered, washed with acetone and left to dry before being used as carbamoylation catalyst.

With this catalyst (148 mg) the reaction of 2,4-toluenediamine (97.3 mg) is carried out in dimethyl carbonate (2.226 g) in a vial which can withstand pressure during 8 h.

After this time, the mixture is left to cool and after reaching atmospheric pressure is opened. The filtered liquid contains a mixture of the dicarbamoylated product in 84% and mixture of the ortho and para mono carbamoylated isomers in 16%. The formation of products derived from N-methylation was not observed.

The invention claimed is:
1. A process for preparing a carbamate, comprising a reaction between:
   an amine or a polyamine,
   an organic carbonate of formula (OR)(OR')C=O, wherein R and R' are independently selected from alkyl group having 1 to 20 carbon atoms, a substituted aryl group, or a non-substituted aryl group, and a catalyst comprising a metal selected from group 8, 9, 10 or 11 of the periodical system placed onto cerium oxide, wherein the particle size of the catalyst is between 1 and 50 nm.

2. The process according to claim 1, wherein the metal is a metal selected from groups 9, 10 and 11 of the periodical system.

3. The process according to claim 1, wherein the metal is selected from among Fe, Cu, Ag, Pd, Pt, Ni, Co, Rh, Ir, Au, and a combination thereof.

4. The process according to claim 3, wherein the metal is selected from among Cu, Ag, Pd, Pt, Ni, Co, Rh, Ir, Au, and a combination thereof.

5. The process according to claim 4, wherein the metal is Au.

6. The process according to claim 1, wherein the metal is found in a percentage between 0.01 and 10% by weight.

7. The process according to claim 6, wherein the metal is found in a percentage between 0.1 and 6% by weight.

8. The process according to claim 1, wherein the metal has a particle size between 1 and 20 nm.

9. The process according to claim 8, wherein the metal has a particle size between 2 and 10 nm.

10. The process according to claim 1, wherein the carbonate is dimethyl carbonate.

11. The process according to claim 1, wherein the carbonate is diethyl carbonate.

12. The process according to claim 1, wherein R and R' are fluorinated alkyl groups.

13. The process according to claim 12, wherein the carbonate is selected from among bis(2-fluoroethyl) carbonate, bis(3-fluoropropyl) carbonate, bis(2,2,2-trifluoroethyl) carbonate, bis(1,3-difluoro-2-propyl) carbonate, bis(1,1,1-trifluoro-2-propyl) carbonate, bis(2,2,3,3-tetrafluoro propyl) carbonate, bis(2,2,3,3,3-pentafluoropropyl) carbonate, bis(1-fluoro-2-butyl) carbonate, bis(2-fluoro-1-butyl) carbonate, bis(1-fluoro-2-methyl-2-propyl) carbonate, bis(2-fluoro-2-methyl-1-propyl) carbonate, bis(1H,1H,2H,2H-perfluoro-1-hexyl) carbonate, bis(perfluorooctyl) carbonate, and bis(1,1,1,3,3,3-hexafluoro-2-propyl) carbonate.

14. The process according to claim 13, wherein the carbonate is bis(2,2,2-trifluoroethyl) carbonate.

15. The process according to claim 1, wherein the amine or the polyamine is an amine of formula $R(NH_2)_n$ where R is selected from among substituted or non-substituted alkyl with 1 to 20 carbon atoms, substituted or non-substituted aryl with 6 to 15 carbon atoms, substituted or non-substituted arylalkyl with 7 to 15 carbon atoms, substituted or non-substituted alkenyl with 2 to 20 carbon atoms, substituted or non-substituted alkynyl with 2 to 20 carbon atoms, substituted or non-substituted cycloalkyl with 3 to 20 carbon atoms, substituted or non-substituted cycloalkenyl with 4 to 20 carbon atoms and substituted or non-substituted cycloalkynyl with 5 to 20 carbon atoms; and n is 1, 2, 3, 4, 5 or 6.

16. The process according to claim 15, wherein the amine or the polyamine is selected from among n-propylamine, isopropylamine, n-butylamine, n-hexylamine, n-octylamine, laurylamine, cyclopentylamine, cyclohexylamine, cyclooctylamine, 1,2-diaminoethane, 1,12-diaminododecane, 1,4-diaminocyclohexane, 1,3-bis(aminomethyl)cyclohexane, 1,4-bis(aminomethyl)cyclohexane, hydrogenated 2,4-diaminodiphenylmethane, hydrogenated toluenediamine, aniline, benzylamine, 2-aminotoluene, 4-aminotoluene, 2,4'-diaminodiphenylmethane, 4,4'-diaminodiphenylmethane, 2,2'-diaminodiphenylmethane, 2,4-toluenediamine, 2,6-toluenediamine, m-phenylendiamine, 1,5-diaminonaphthalene and mixtures thereof.

17. The process according to claim 1, further comprising:
transforming the carbamate to its corresponding isocyanate.

* * * * *